(12) United States Patent
Puttlitz et al.

(10) Patent No.: US 8,945,185 B2
(45) Date of Patent: Feb. 3, 2015

(54) INTERSPINOUS SPACER DEVICES FOR DYNAMIC STABILIZATION OF DEGRADED SPINAL SEGMENTS

(75) Inventors: Christian M. Puttlitz, Fort Collins, CO (US); Benjamin C. Gadomski, Fort Collins, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 0 days.

(21) Appl. No.: 13/983,036

(22) PCT Filed: Sep. 2, 2011

(86) PCT No.: PCT/US2011/050370
§ 371 (c)(1),
(2), (4) Date: Jul. 31, 2013

(87) PCT Pub. No.: WO2012/106014
PCT Pub. Date: Aug. 9, 2012

(65) Prior Publication Data
US 2013/0317549 A1    Nov. 28, 2013

Related U.S. Application Data

(60) Provisional application No. 61/438,719, filed on Feb. 2, 2011.

(51) Int. Cl.
*A61B 17/70* (2006.01)
(52) U.S. Cl.
CPC ......... *A61B 17/7067* (2013.01); *A61B 17/7038* (2013.01); *A61B 17/7055* (2013.01)
USPC .......................................... 606/249; 606/248
(58) Field of Classification Search
USPC .................. 606/248, 249, 252, 256–259, 282
See application file for complete search history.

(56) References Cited

U.S. PATENT DOCUMENTS

| 5,562,663 | A | 10/1996 | Wisnewski et al. |
| 2005/0187548 | A1 | 8/2005 | Butler et al. |
| 2006/0161157 | A1 | 7/2006 | Mosca et al. |
| 2006/0293662 | A1* | 12/2006 | Boyer et al. .................... 606/61 |
| 2007/0016200 | A1 | 1/2007 | Jackson |
| 2008/0195154 | A1* | 8/2008 | Brown et al. ................. 606/257 |
| 2008/0249528 | A1 | 10/2008 | Khalife |
| 2009/0030465 | A1* | 1/2009 | Altarac et al. ................ 606/257 |
| 2009/0149885 | A1* | 6/2009 | Durward et al. .............. 606/246 |
| 2009/0254122 | A1 | 10/2009 | Khalife |
| 2010/0010542 | A1 | 1/2010 | Jackson |
| 2010/0152787 | A1 | 6/2010 | Walsh et al. |
| 2010/0174319 | A1 | 7/2010 | Jackson |
| 2010/0198272 | A1 | 8/2010 | Keyer et al. |

OTHER PUBLICATIONS

International Search Report and Written Opinion, PCT Application No. PCT/US2011/050370, mailed Dec. 23, 2011, 7 pages.

(Continued)

*Primary Examiner* — Eduardo C Robert
*Assistant Examiner* — Julianna N Harvey
(74) *Attorney, Agent, or Firm* — Polsinelli PC

(57) ABSTRACT

An interspinous spacer device for the treatment of high-grade spinal disorders is disclosed herein. The interspinous spacer device includes a sliding rod and a base that contains a curved internal track that limits the range of motion and center of rotation of the spinal segments stabilized using the device to the physiological levels of a nondegraded spinal segment.

18 Claims, 13 Drawing Sheets

(56) References Cited

OTHER PUBLICATIONS

International Search Report and Written Opinion, PCT Application No. PCT/US2011/050358, mailed Dec. 23, 2011, 9 pages.

Bastian et al. *Evaluation of the mobility of adjacent segments after posterior thoracolumbar fixation: a biomechanical study.* European Spine Journal (2001) 10:295-300.

Cheh et al. *Adjacent Segment Disease following Lumbar/Thoracolumbar Fusion with Pedicle Screw Instrumentation.* Spine (2007) vol. 32, No. 20, pp. 2253-2257.

Chow et al. *Effects of Short Anterior Lumbar Interbody Fusion on Biomechanics of Neighboring Unfused Segments.* Spine (1996) vol. 21, No. 5, pp. 549-555.

Cossette et al. *The Instantaneous Center of Rotation of the Third Lumbar Intervertebral Joint.* Journal of Biomechanics (1971) vol. 4, pp. 149-153.

Kettler et al. *Finite helical axes of motion are a useful tool to describe the three-dimensional in vitro kinematics of the intact, injured and stabilised spine.* European Spine Journal (2004) 13:553-559.

Korovessis et al. *Does Wallis implant reduce adjacent segment degeneration above lumbosacral instrumented fusion?* European Spine Journal (2009) 18:830-840.

Nagata et al. *The Effects of Immobilization of Long Segments of the Spine on the Adjacent and Distal Facet Force and Lumbosacral Motion.* Spine (1993) vol. 18, No. 16, pp. 2471-2479.

Niosi et al. *Biomechanical characterization of the three-dimensional kinematic behaviour of the Dynesys dynamic stabilization system: an in vitro study.* European Spine Journal (2006) 15:913-922.

Ogston et al. *Centrode Patterns in the Lumbar Spine: Baseline Studies in Normal Subjects.* Spine (1986) vol. 11, No. 6, pp. 591-595.

Pennal et al. *Motion Studies of the Lumbar Spine: A Preliminary Report.* The Journal of Bone and Joint Surgery (1972) vol. 54B, No. 3, pp. 442-452.

Penning et al. *Instability in Lumbar Spondylolisthesis: A Radiologic Study of Several Concepts.* American Roentgen Ray Society 134:293-301, Feb. 1980.

Press Release. *KYPHON Ahead of the Curve: Kyphon and the X-STOP® Procedure to be Featured on American Health Radio on Monday, Apr. 2, 2007.* PR Newswire Mar. 29, 2007 (http://www.prnewswire.com/mnr/kyphon/27585/).

Rousseau et al. *The instant axis of rotation influences facet forces at L5/S1 during flexion/extension and lateral bending.* European Spine Journal (2006) 15:299-307.

Sakamaki et al. *Normal and Spondylolytic Pediatric Spine Movements with Reference to Instantaneous Axis of Rotation.* Spine (2002) vol. 27, No. 2, pp. 141-145.

Schmidt et al. *Interaction Between Finite Helical Axes and Facet Joint Forces Under Combined Loading.* Spine (2008) vol. 33, No. 25, pp. 2741-2748.

Sengupta D K. *Dynamic stabilization devices in the treatment of low back pain.* Neurol India (2005) 53:466-74.

Vaga et al. *Molecular MR imaging for the evaluation of the effect of dynamic stabilization on lumbar intervertebral discs.* European Spine Journal (2009) 18 (Suppl 1):S40-S48.

Weinhoffer et al. *Intradiscal Pressure Measurements Above an Instrumented Fusion.* Spine (1995) vol. 20, No. 5, pp. 526-531.

U.S. Appl. No. 13/983,020, filed Jul. 31, 2013, Puttlitz et al.

\* cited by examiner

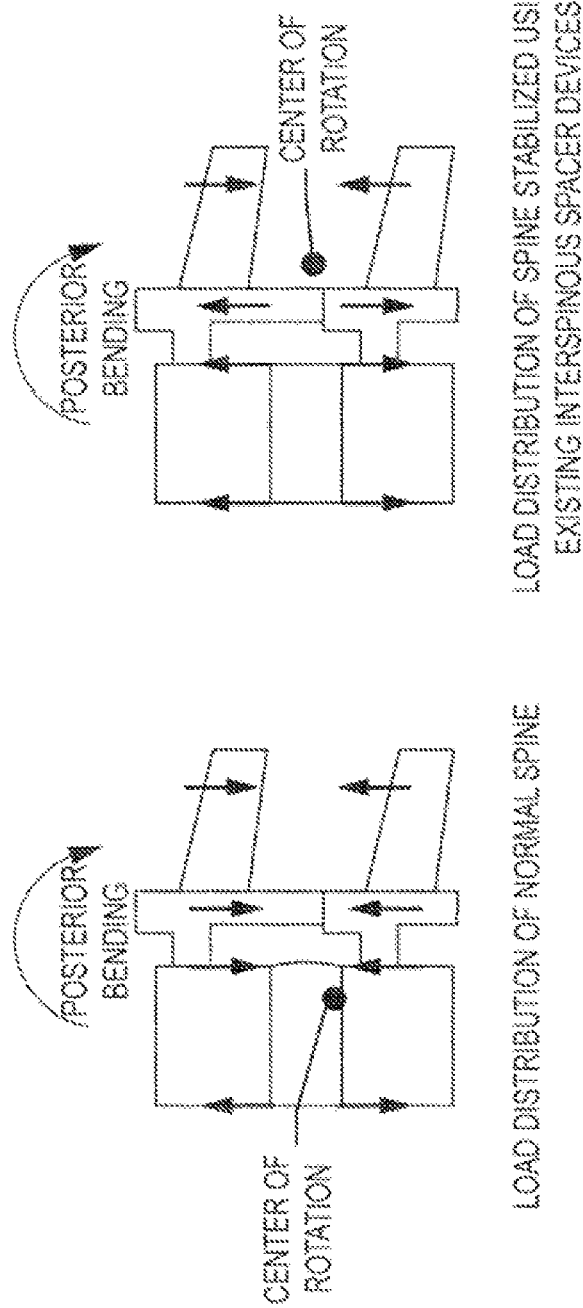

INTERSPINOUS SPACER DEVICES FOR DYNAMIC STABILIZATION OF DEGRADED SPINAL SEGMENTS

CROSS REFERENCE TO RELATED APPLICATIONS

This Patent Cooperation Treaty (PCT) patent application incorporates in its entirety and claims the benefit under 35 U.S.C. §119(e) of: U.S. Provisional Application 61/438,719, filed Feb. 2, 2011 and titled "Dynamic Stabilization Device for the Manipulation of the Axis of Rotation of the Lumbar Spine and Correction of the Center of Rotation in the Lumbar Spine".

The present application is related to PCT International Patent Application No. PCT/US2011/050358, which is entitled "Pedicle Screw Assembly and Dynamic Stabilization Devices Incorporating the Pedicle Screw Assembly", filed 2 Sep. 2011, and incorporated by reference in its entirety into the present application.

FIELD OF THE INVENTION

The present invention relates to devices for the treatment of high-grade spinal disorders. More specifically, the present invention relates to interspinous spacer devices.

BACKGROUND OF THE INVENTION

Posterolateral fusion is the standard procedure for treating high grade spinal disorders such as spinal stenosis as well as spondylolisthesis. Despite the wide-spread use of posterolateral fusion as a surgical approach for correcting back pain, numerous problems have been associated with its use. Spinal fusion recipients may be at risk for developing Adjacent Segment Disease (ASD), a condition in which the motion segments adjacent to the fused vertebral segments experience higher rates of degeneration deterioration due to an increase in vertebral loading, higher intradiscal pressures, increased range of motion, and increased facet motion.

Dynamic spinal stabilization has recently emerged as an alternative procedure to treat many degenerative spinal disorders. Existing dynamic stabilization devices restore stability to an injured spine while simultaneously allowing a restricted range of motion. These devices are designed to preserve the integrity of adjacent segments by minimizing the transfer of segment motion and facet joint forces between the stabilized spinal segment and the adjacent spinal segments.

Existing dynamic spine stabilization devices incorporate selectively flexible elements such as flexible cords and intervertebral spacers, or flexible spring rods in order to allow a constrained range of motion to the stabilized spinal segment. To date, no existing dynamic spine stabilization device constrains the rotation of the stabilized segments to a center of rotation that is coincident with a physiological center of rotation. Physiologically representative loading of a spinal segment that is stabilized using a dynamic stabilization device is unlikely to occur unless the rotational motion of the spinal segment passes through the spine's natural center of rotation. The imposition of a non-physiological center of rotation location by existing dynamic stabilization devices may result in alterations to the physiological pattern of tissue stresses and may further increase the likelihood of hardware failure. These altered tissue stresses and non-physiological motion patterns may also be induced in adjacent motion segments, increasing the likelihood of long-term complications, such as ASD, associated with existing stabilization procedures.

In addition, at least some of the existing dynamic spine stabilization devices incorporate pedicle screws in their design. However, the treatment of back pain using pedicle-based implants may pose an increased risk of complications in certain patient populations. To address potential risks of the treatment of back pain using pedicle screw-based stabilization devices, interspinous spacer devices may be used to correct spinal stenosis and facet arthrosis when a less invasive surgical procedure is preferred or when pedicle screw use is unsuccessful.

Interspinous spacers are an appropriate treatment for patients experiencing neurogenic pain that is relieved in flexion and exacerbated in extension. Existing interspinous spacer designs aim to unload the intervertebral disc and increase the neuroforaminal height by limiting the amount of motion available during extension. These existing interspinous spacers typically focus closely on the stabilization of extension movements while neglecting lateral bending, axial rotation, and sometimes even flexion movements. As a result, many existing interspinous spacer devices provide limited stability in lateral bending and axial rotation. A variety of attachment methods are used for existing interspinous spacer devices including polyester tethers and metal clamps, and it is unclear how these fasteners may influence the motion segment's center of rotation during spinal flexion movements. In addition, device slippage and spinous process failure are potential complications associated with the use of existing interspinous spacer devices.

There is a need in the art for an interspinous spacer device that not only allows limited motion of injured or deteriorated vertebral segments, but that constrains that motion to a range that is consistent with the range of motion of the corresponding normal healthy vertebrae. In particular, a need exists for an interspinous spacer device in which the degraded vertebrae are constrained to rotate about an axis that is consistent with a normal healthy spine.

BRIEF SUMMARY OF THE INVENTION

In one embodiment, an interspinous spacer device for the stabilization of a degraded spinal segment is disclosed herein. The interspinous spacer device includes a base and a sliding rod. The base includes a body containing a curved internal track that opens upward into an aperture contained within an upper surface of the body. The aperture has an aperture cross-sectional area that is smaller than a corresponding track cross-sectional area of the track. The sliding rod includes a retaining plate situated within the track as well as a column attached to the retaining plate. The retaining plate has a plate cross-sectional area that is larger than the aperture cross-sectional area and smaller than the track cross-sectional area. The column includes an upper column end and a lower column end opposite to the upper column end. The lower column end is attached to the retaining plate and the upper column end protrudes upward through the aperture and out of the upper surface of the body. The retaining plate of the sliding rod freely slides within the track to actuate an arcuate movement of the sliding rod along a range of movement limited by a length of the track. The center of rotation of the arcuate movement is situated at a perpendicular distance from the track that is equal to a radius of curvature of the track.

In another embodiment, an interspinous spacer device for the stabilization of a degraded spinal segment is disclosed herein. The interspinous spacer device includes a base and a sliding rod. The base includes a body containing a curved internal track that is bounded at opposite ends by a lower track wall and an upper track wall, and bounded laterally by a curved anterior track wall, a curved posterior track wall, and two side track walls. The track opens upward into an aperture contained within the track upper wall that extends through an upper surface of the body. The aperture has an aperture cross-sectional area that is smaller than a corresponding track cross-sectional area of the track. The sliding rod includes a retaining plate situated within the track. The retaining plate includes an upper surface, a lower surface, an anterior face, a posterior face, and two side faces. The retaining plate has a plate cross-sectional area that is larger than the aperture cross-sectional area and smaller than the track cross-sectional area.

In this embodiment, the column includes a lower column end attached to the upper surface of the retaining plate and an upper column end situated opposite to the lower column end and protruding upward from the upper surface of the body through the aperture of the body. The retaining plate of the sliding rod slides freely within the track to actuate an arcuate movement of the sliding rod along a range of movement limited by the track. The center of rotation of the arcuate movement is situated at a perpendicular distance from the anterior track wall that is equal to a radius of curvature of the track.

While multiple embodiments are disclosed, still other embodiments of the present invention will become apparent to those skilled in the art from the following detailed description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

BRIEF DESCRIPTION OF THE DRAWINGS

FIGS. 1A and 1B are schematic drawings of the load distribution on a normal vertebral segment (FIG. 1A) and on a vertebral segment constrained to rotate about a different center of rotation by a dynamic stabilization device.

Corresponding reference characters indicate corresponding elements among the views of the drawings. The headings used in the figures should not be interpreted to limit the scope of the claims.

DETAILED DESCRIPTION

Figure 2B:
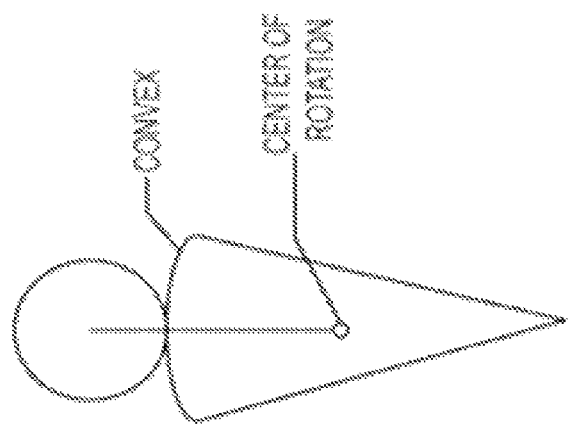
FIGS. 2A and 2B are drawings illustrating the effect of concave (FIG. 2A) versus convex (FIG. 2B) curvature of interspinous spacer device surfaces on the location of its center of rotation.

Interspinous spacer devices for the relief of conditions including but not limited to spinal stenosis and facet arthrosis are disclosed herein. Embodiments of the interspinous spacer devices increase the neuroforaminal height between two vertebrae by limiting the motion segment's rotation in extension while preserving physiologic loading of the vertebrae in flexion by projecting the motion segment's center of rotation to the segment's natural, undegenerated location. Further, the embodiments of the interspinous spacer devices restore the stresses of overloaded facet joints to natural, undegenerated levels. The design of embodiments of the interspinous spacer devices also increase stability in the transverse and coronal planes by secure attachment to the spinous processes while limiting the stresses experienced at these interfaces.

a. Principle of Design

Embodiments of the interspinous spacer devices provide enhanced structural support to compensate for degenerated spinal structures while simultaneously preserving a range of motion that is comparable to the natural motion of the undegenerated spinal segment. A critical factor governing the motion and segment loading of a stabilized spinal segment is the location of the center of rotation of the stabilized segment.

Center of rotation, as used herein, describes the spatial location of an axis of rotation about which two adjacent vertebrae rotate relative to one another in the course of an overall rotation of the spine. The overall rotation of the spine may occur as the result of any number of movements including but not limited to dorso-ventral flexion and extension, lateral bending to the left or right, axial rotation (twisting) and any combination thereof. In order to accomplish any of these overall movements, individual adjacent vertebrae rotate relative to one another in a variety of directions. In the process of these movements, loads are also transmitted between adjacent vertebrae in a characteristic pattern.

FIG. 1A is a schematic diagram illustrating the center of rotation and load distribution between two adjacent vertebrae of a healthy spine during an overall posterior extension movement. Typically, the center of rotation is located somewhere within the anterior portion of the spine as shown in FIG. 1A. This center of rotation further results in tensile loading in those regions of the vertebra anterior to the center of rotation and compressive loads in those regions posterior to the center of rotation.

Existing interspinous spacer devices may include a hinge or other rotating element in the region posterior to the vertebral disks due to the constraints imposed by the task of implanting structurally reinforcing devices onto posterior spinal structures using existing surgical procedures. As a result, the center of rotation of a spinal segment stabilized using existing interspinous spacer devices may have centers of rotation that are shifted significantly in a posterior direction, as illustrated in FIG. 1B. In addition, the loading pattern between the two adjacent vertebrae may be altered such the vertebra experience tensile loading over a significantly larger proportion of their anterior regions, and significantly less compressive loading during the posterior extension movement illustrated in FIG. 1B.

The instantaneous center of rotation (ICR) in the lumbar motion segment in the neutral posture is typically located slightly posterior of the center of the intervertebral disc in a normal spine. Although the ICR shifts in an anterior and superior direction during spinal flexion and in a posterior direction during extension, the ICR typically remains situated within the disc or within the upper aspect of the inferior vertebra. Greater variations in the location of the ICR during movement are known to appear in degenerated spines. This occurrence of the ICR outside normal physiological limits has been associated with spinal pathology.

In order to preserve the vertebral center of rotation at its natural location, embodiments of the interspinous spacer devices project the center of rotation to a location that is anterior of the device's implanted location. This anterior projection of the center of rotation is accomplished by configuring the geometry of the device such that the rotation does not occur along an internal axis. The concept by which embodiments of the interspinous spacer devices disclosed herein project the center of rotation in an anterior direction is illustrated in FIG. 2.

Figure 2A:
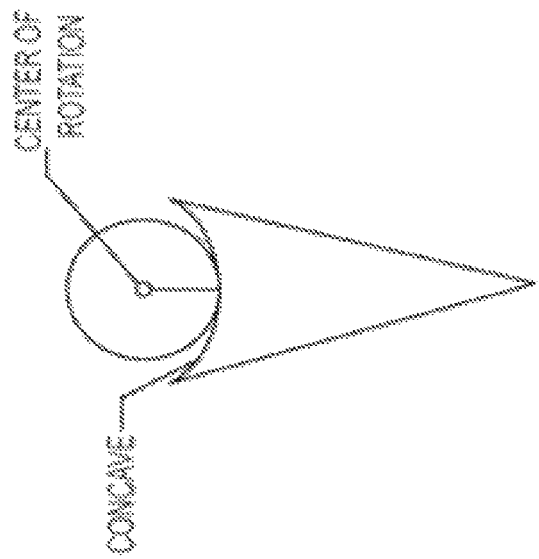

FIGS. 2A and 2B illustrate a round ball that is free to roll on either a concave or a convex surface, respectively. As shown in FIG. 2A, a round ball that rolls on a concave surface will rotate around a center of rotation in the geometric center of the ball. The cup-like concave surface cradles the ball and projects the axis of rotation back into the rolling ball. However, if the same ball rolls on a convex surface as shown in FIG. 2B, the center of rotation is projected downward and away from the ball.

Embodiments of the interspinous spacer devices incorporate this concept of center of rotation projection as a basis for the device's design. By utilizing curved surfaces with a specific radius, the device may be configured such that the center of rotation of the stabilized spinal segment is projected back into the anterior portion of the spine. Embodiments of the devices make use of a sliding motion for device movement rather than the conventional rotation of internal hinged elements typical of existing interspinous spacer devices. The anterior distance that the center of rotation is projected from embodiments of the device may be controlled by altering the radius of the curved surfaces inside of the device.

b. Interspinous Spacer Devices

Figure 3:
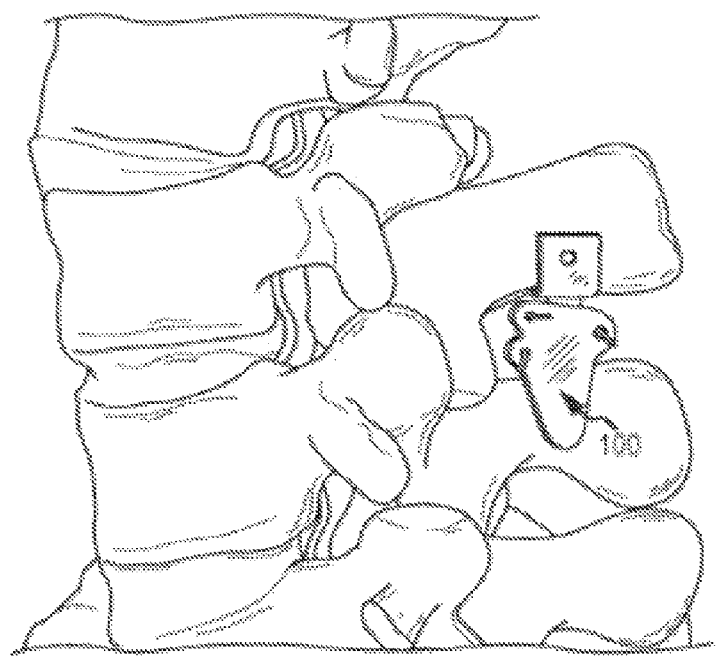
FIG. 3 is a photograph of a prototype interspinous spacer device installed between the spinous processes of two lumbar vertebrae.

An embodiment of an interspinous spacer device 100 is shown fitted between two spinous processes of a spine segment model in FIG. 3. The interspinous spacer device 100 may be affixed to the spinous processes using existing surgical fasteners suitable for orthopedic surgical applications including but not limited to pin connectors. The interspinous spacer device 100 may maintain a minimum spacing during extension in order to increase the neuroforaminal height relative to the degraded segment, and may also constrain the center of rotation of the segment to be coincident with the center of rotation of an undegraded segment during other movements, including but not limited to flexion, axial twisting, and lateral bending.

The interspinous spacer device 100 overcomes many of the limitations of existing interspinous spacer devices. Because the interspinous spacer device 100 includes only two moving parts, the likelihood of failure may be substantially lower. Further, the close proximity of the interspinous spacer device 100 to the spinal column's natural line of loading may result in lower stresses on the interspinous spacer device 100 and the spinal processes to which the device 100 are attached, further reducing the likelihood of failure of the device 100 or fracture of the spinal processes to which the device 100 is attached.

Figure 4:
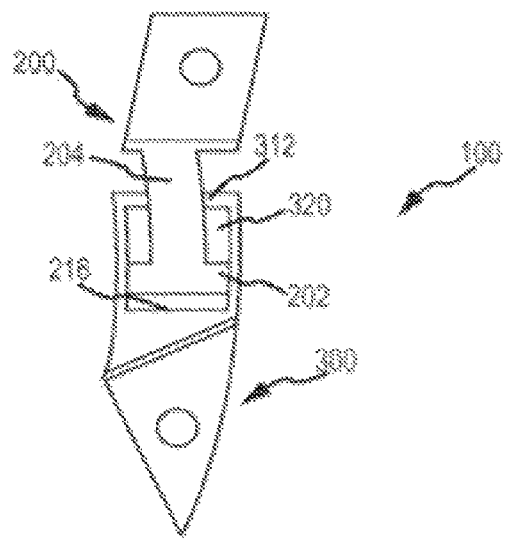
FIG. 4 is a side sectional view of an interspinous spacer device.
Figure 5:
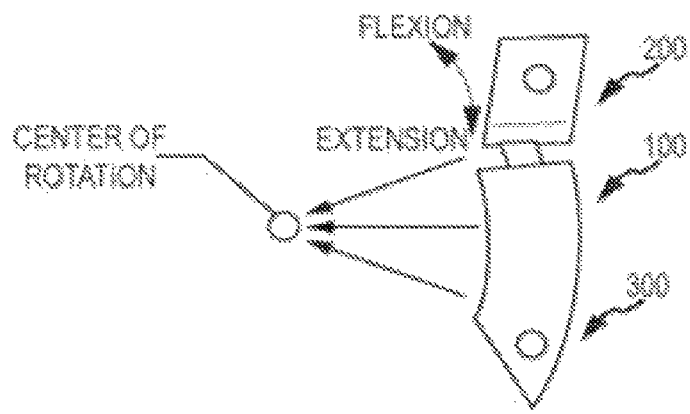
FIG. 5 is a drawing showing the arcuate movement of a sliding rod within a base of an interspinous spacer device and the resulting center of rotation of the movement.

Referring to FIG. 4, the interspinous spacer device 100 comprises an outer base 300 that attaches to the caudal spinous process and an upper sliding rod 200 that attaches to the cranial spinous process. The sliding rod 200 is free to slide relative to the base 300 through a distance limited by the dimensions of the base 300. All sliding surfaces of the interspinous spacer device 100 may possess a curvature, thereby constraining the movement of the sliding rod 200 to an arcuate movement, resulting in the projection of the center of rotation of the moving segment in an anterior direction during flexion, as illustrated in FIG. 5.

i. Sliding Rod

Referring back to FIG. 4, the sliding rod 200 may include an enlarged retaining plate 202 situated on the lower end 216 of the sliding rod 200. The retaining plate 202 prevents the sliding rod 200 from separating away from the base 300 during maximum separation of the vertebral processes to which the interspinous spacer device 100 is attached, such as may occur during maximum spinal flexion. By limiting the maximum extension of the sliding rod 200 out of the base 300, the retaining plate 202 imposes a hard limit on the maximum rotation of the spinal segment during flexion.

The retaining plate 202 may have any non-circular cross-sectional shape, so long as the cross-sectional shape of the retaining plate 202 is matched to the cross-sectional shape of the track, and is shaped such that the sliding rod 200 is constrained against freely rotating about an axis coincident with the direction of sliding. The cross-sectional dimensions of the retaining plate 202 are sized to be consistent with the cross-sectional dimensions of the corresponding track 320 contained within the base 300. In an embodiment, the cross-sectional dimensions and the thickness of the retaining plate 202 may be specified in order to impart a desired range of motion to the interspinous spacer device 100 in use. For example, if the cross-sectional dimensions of the retaining plate 202 are significantly smaller than the corresponding dimensions of the track, the range of movement of the spinal segment stabilized by the interspinous spacer device 100 may be enhanced due to the increased degree of movement or "play" of the sliding rod 200 within the track 320 perpendicular to the direction of sliding. Similarly, a thicker retaining plate 202 may increase the contact area between the retaining plate 202 and the sides of the track 320, thereby reducing the amount of play of the sliding rod 200 within the track 320 and resulting in a reduced range of motion of the interspinous spacer device 100. A thicker retaining plate 202 may also reduce the maximum extension of the sliding rod 200 from the base 300.

Figure 6:
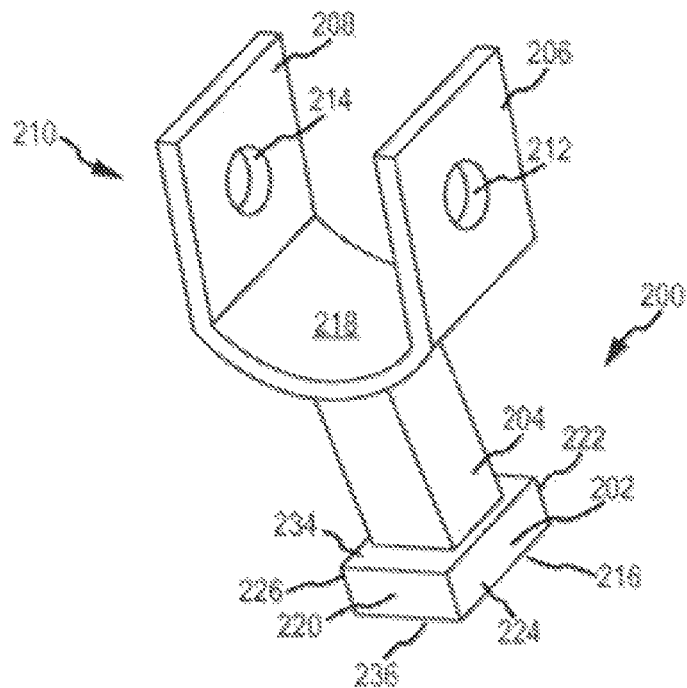
FIG. 6 is a perspective view of a sliding rod of an interspinous spacer device.

Referring to FIG. 6, the retaining plate 202 includes an upper surface 234, a lower surface 236, an anterior face 220, a posterior face 222, and two side faces 224 and 226. The side faces 224 and 226 provide lateral support to the sliding rod 200 as it slides along the track 320. The anterior face 220 and posterior face 222 slide along the curved portions of the track 320, imparting the arcuate sliding motion to the sliding rod 200. In an embodiment, the anterior face 220 and the posterior face 222 may be curved such the radius of curvature of each face is matched to the radius of curvature of the corresponding surfaces of the track 320.

The sliding rod 200 further includes a column 204 attached at its lower column end to the upper surface 234 of the retaining plate 202, and to the cranial attachment fitting 210 at its opposite upper column end. The column 204 is a rigid structure capable of sustaining, without significant deformation, the loads imposed by the cranial vertebra to which the sliding rod 200 is attached and by the caudal vertebra to which the base 300 is attached. The column 204 may be any cross-sectional shape and dimension, so long as the column 204 fits within the track 320 without interfering with the sliding movement of the sliding rod 200 and the column 204 is able to slide smoothly through the aperture 312 of the base (see FIG. 4). In an embodiment, the cross-sectional shape of the column 204 is matched to the cross-sectional shape of the aperture 312 and the cross-sectional dimensions of the column 204 are slightly smaller than the corresponding cross-sectional dimensions of the aperture 312. In another embodiment, the cross-sectional shape of the column 204 is matched to the cross-sectional shape of the track 320 in order to maintain all surfaces of the column 204 at a fixed distance away from the surfaces of the track 320.

Figure 7:
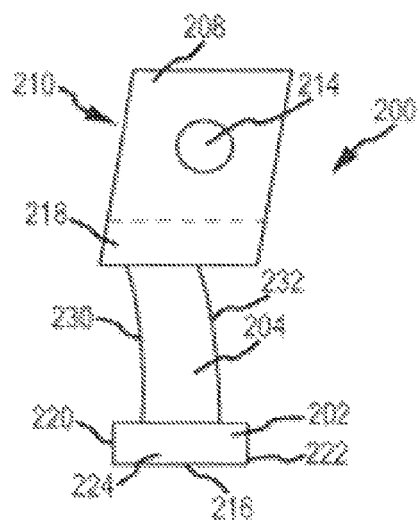
FIG. 7 is a side view of a sliding rod of an interspinous spacer device.

Referring to FIG. 7, the anterior column surface 230 and posterior column surface 232 may be any shape, so long as these surfaces do not interfere with the sliding movements of the sliding rod 200 within the base 300. In an embodiment, the anterior column surface 230 and posterior column surface 232 may have a radius of curvature that is matched to the corresponding surfaces of the track 320 within the base 300.

Referring back to FIG. 6, the cranial attachment fitting 210 is attached to the upper column end opposite to the retaining plate 202. The cranial attachment fitting 210 is shaped to fit around a vertebral process cranial to a degraded spinal segment. The cranial attachment fitting 210 includes a lower plate 218 and two lateral plates 206 and 208 that are attached to the lateral edges of the lower plate 218 such that they project upward from the lower plate. The lateral plates 206 and 208 also contain two cranial fastener holes 212 and 214.

A spinal process cranial to a degraded spinal segment may be situated within the groove formed by the lateral side plates 206 and 208 and the lower plate 218, and fasteners may be inserted through the cranial fastener holes 212 and 218 into the spinal process in order to fasten the cranial attachment fitting 210 to the spinal process. Any known fastener may be used to attach the cranial attachment fitting 210 to the spinal process, including but not limited to surgical-grade pins, screws, bolts, and any combination thereof.

In an embodiment, any or all curved sliding surfaces of the sliding rod 200 may have a radius of curvature of about 50 mm in order to situate the center of rotation of the stabilized spinal segment anteriorly into the intervertebral disc of that segment. Non-limiting examples of curved sliding surfaces of the sliding rod 200 include the anterior face 220 and posterior face 222 of the retaining plate 202, the anterior column surface 230 and the posterior column surface 232. In another embodiment, the thickness of the retaining plate 202 may be about 3.5 mm.

ii. Base

Figure 8:
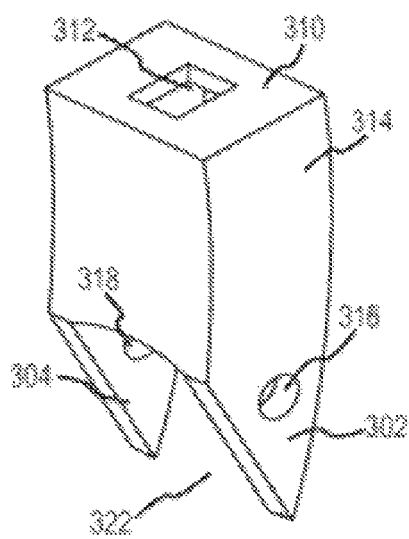
FIG. 8 is a perspective view of a base of an interspinous spacer device.

Referring to FIG. 8, the base 300 includes a body 314 containing the track 314 (not shown) within which the sliding rod 200 slides. Caudal attachment plates 302 and 304 project downward from opposite edges of the body 314, forming a caudal attachment fitting 322. A spinal process caudal to the segment to be stabilized may be situated within the groove formed by the caudal attachment plates 302 and 304 and the lower surface 318 of the body 314. Fasteners may be inserted through the caudal fastener holes 316 and 318 into the caudal spinal process in order to fasten the caudal attachment fitting 322 to the caudal spinal process. Any known fastener may be used to attach the caudal attachment fitting 322 to the caudal spinal process, including but not limited to surgical-grade pins, screws, bolts, and any combination thereof.

The body 314 of the base 300 contains an internal track (not shown) that opens to an aperture 312 on the upper surface 310 of the base 300. The aperture 312 may have any non-circular cross-sectional shape and dimension, so long as the aperture 312 allows the column 204 of the slider rod 200 to slide in and out of the base 300 without significant friction, resistance, locking, sticking, or seizing. Further, the cross-sectional shape and dimension of the aperture 312 may be significantly smaller than the corresponding cross-sectional dimensions of the retaining plate 202 so that the retaining plate cannot pass through the aperture 312, thereby constraining the full extension of the sliding rod 200 from the base 300.

Figure 9:
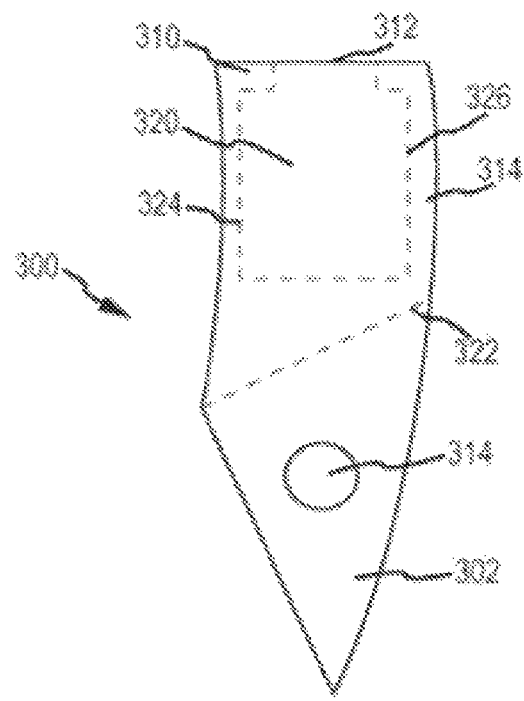
FIG. 9 is a side view of a base of an interspinous spacer device.

Referring to FIG. 9, the base 300 contains an internal curved track 320 surrounded by the outer surface of the body 314. The curved track 314 includes a curved anterior track wall 324 and a curved posterior track wall 326, as well as two flat lateral track walls. The anterior face 220 of the retaining plate 202 may slide along the curved anterior track wall 324, the posterior face 222 of the retaining plate 202 may slide along the curved posterior track wall 326, and two side faces 224 and 226 of the retaining plate 202 may slide along the two lateral track walls.

The shape and dimensions of the curved track 320 are critical aspects of the design of the interspinous spacer device 100. The height of the track 320 limits the range of rotational movement of the stabilized spinal segment to within a physiological range corresponding to the movements of normal healthy vertebrae. The curvature of the track 320 projects the center of rotation of the stabilized vertebra to a location consistent with the center of rotation of corresponding normal, healthy vertebrae. In one aspect, the radius of curvature of the track 320 is essentially equal to the distance between the anterior track surface 324 and the center of rotation of the stabilized vertebra.

In one embodiment, the radius of curvature of the anterior track wall 324 and a posterior track wall 326 are about 50 mm in order to situate the center of rotation of the stabilized spinal segment anteriorly into the intervertebral disc of that segment. In another embodiment, the height of the curved track 320 is about 7.0 mm and the thickness of the retaining plate is about 3.5 mm. In this embodiment, the resulting interspinous spacer device 100 has a range of motion that includes a fully extended position of the sliding rod 200 from the base 300 of about 3.5 mm relative to fully retracted position, corresponding to a maximum of about 8.0° of rotation of the supported spinal segment during spinal flexion.

c. Applications of Interspinous Spacer Devices

Embodiments of the interspinous spacer devices 100 may be used for the treatment of high grade spinal disorders such as spinal stenosis as well as facet arthrosis. The devices 100 may be used to stabilize spinal segments at any location along the spine, including but not limited to the cervical, thoracic, lumbar, and any combination thereof.

The sliding rod 200 of the interspinous spacer device 100 is free to slide inside of the base 300 within a limited range of motion as described above to allow flexion-extension movement. In addition, the interspinous spacer device 100 may be attached to the spinal processes situated cranial and caudal to the degraded spinal segment using fasteners such as surgical pins that may further provide motion within a limited range in lateral bending and axial twisting.

In one embodiment, the interspinous spacer device 100 may be attached to spinous processes of vertebrae that are situated cranial or caudal relative to a degraded motion segment, as shown in FIG. 3. The cranial attachment fitting 210 may be situated around the lower portion of a spinous process of the vertebra situated cranial to the degraded motion segment. One or more surgical fasteners may be inserted through cranial fastener holes 212 and 218 to secure the cranial attachment fitting 210 to the spinous process.

Similarly, the caudal attachment fitting 322 may be attached to a spinous process of a vertebra situated caudal to the degraded motion segment. The caudal attachment fitting 322 may be situated around the upper portion of a spinous process of the vertebra situated cranial to the degraded motion segment. One or more surgical fasteners may be inserted through caudal fastener holes 316 and 318 to secure the caudal attachment fitting 210 to the spinous process.

EXAMPLES

The following examples illustrate various embodiments of the invention.

Example 1

Theoretical Assessment of the Range of Motion of a Stabilized Vertebral Segment Using Finite Element Modeling Computational finite element modeling of the interspinous spacer device using the analysis of a finite element model was performed in order to assess the interspinous spacer device's range of motion.

The base and sliding rod elements of the interspinous spacer device were created in Pro/ENGINEER (Version 5.0, PTC, Needham, Mass.) and imported into ABAQUS (Version 6.9, Simulia, Providence, R.I.) for finite element analysis. The sliding rod and base were meshed with 48,436 and 32,710 eight-node hexahedral brick elements respectively. Ti6Al4V material properties were assigned to each component.

Figure 10:
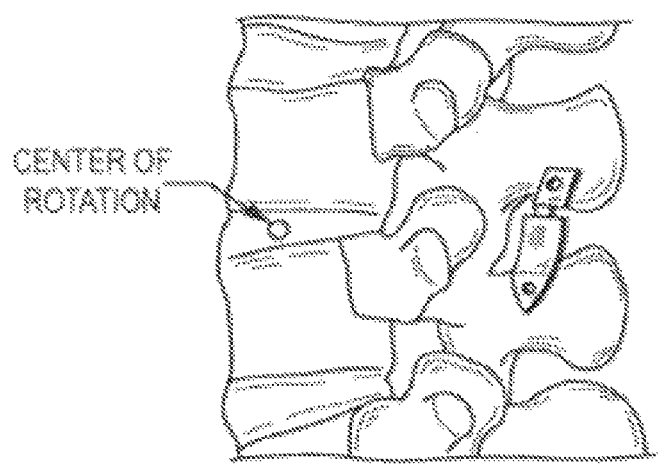
FIG. 10 is an image of a finite element model of an interspinous spacer device implanted in a spinal segment.

A preliminary analysis was performed in order to determine the location of the device's center of rotation. An encastre boundary condition was imposed on the lower face of the base via a kinematic coupling constraint while a superiorly directed tensile force of 150 N was applied to the upper surface of the sliding rod. A reference node situated 50 mm anterior of the device's sliding surfaces was kinematically coupled to the sliding bar in order to track the translation of the center of rotation through the full range of motion of the device. The results of this analysis determined that the center of rotation was situated about 50 mm anterior of the device's sliding surfaces. This anterior location placed the center of rotation directly within the center of the intervertebral disc associated with the stabilized segment, as illustrated in FIG. 10.

Figure 11:
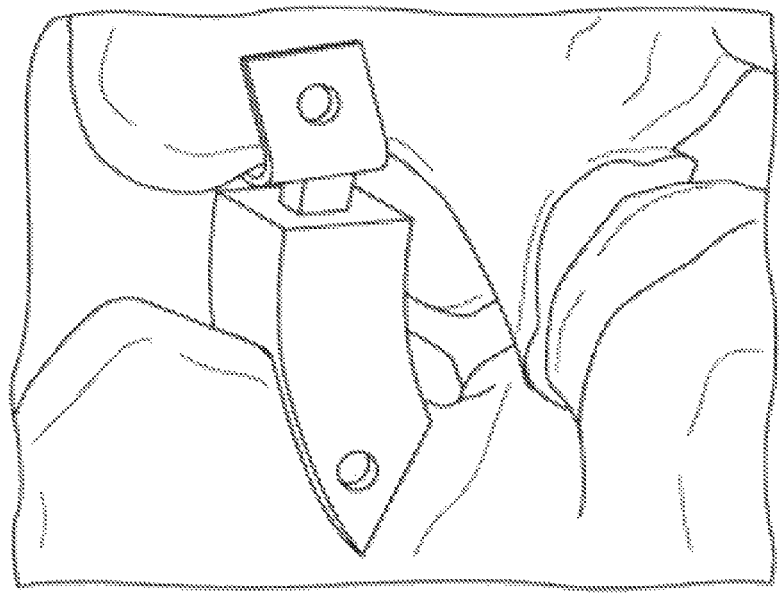
FIG. 11 is an image of a finite element model of an interspinous spacer device implanted in a spinal segment showing the center of rotation during flexion.

The model of the interspinous spacer device was implanted on the L1-L5 lumbar spine model to further assess the range of movement of the stabilized spinal segment and adjacent segments for various conditions of the spinal segment, as illustrated in FIG. 11. An encastre boundary condition was imposed on the inferior L5 endplate while 7.5 Nm flexion/extension moments were applied to the superior endplate of L1. A friction coefficient of 0.3 was specified for the device's sliding surfaces.

The range of motion was assessed for a healthy spine model, an injured spine model with full nucleus pulposus removal at the L2-L3 level, and an injured spine model with the interspinous spacer device implanted. Implantation was modeled between the spinous processes of L2 and L3. The upper and lower components of the device were fastened to the spinous processes via tie constraints.

Figure 12:
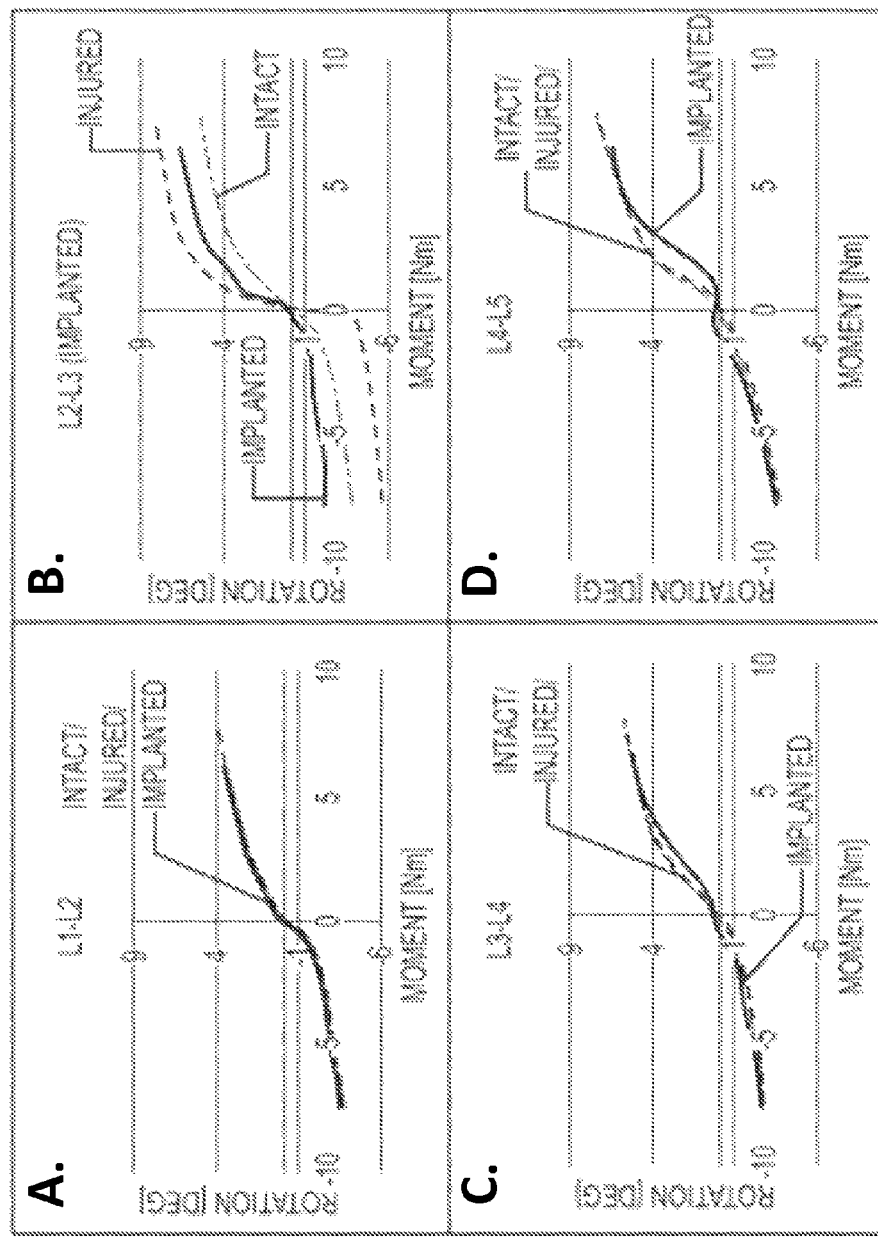
FIGS. 12A-D are graphs showing the relative rotation as a function of applied flexion/extension moment estimated using finite element models during spinal flexion and extension for an intact spine, an injured spine, and an injured spine stabilized with an interspinous spacer device implanted at the L2-L3 level for four different lumbar spine segment levels: L1-L2 (FIG. 12A), L2-L3 (FIG. 12B), L3-L4 (FIG. 12C), and L4-L5 (FIG. 12D).
Figure 13:
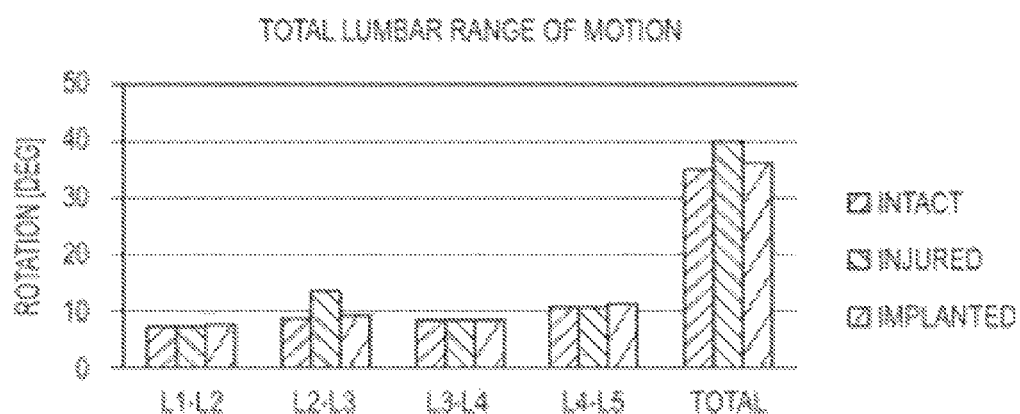
FIG. 13 is a graph comparing the relative rotation of 4 different spinal segment levels and the total lumbar rotation estimated using finite element models during spinal flexion and extension for an intact spine an injured spine, and an injured spine stabilized with an interspinous spacer device implanted at the L2-L3 level.

The range of motion as a function of applied flexion/extension moment determined by the finite element models are summarized in FIG. 12. The rotation of the segment models as well as the total rotation of all segments in response to a 7.5 Nm flexion/extension moment are summarized in FIG. 13. The range of motion for the L1-L2 motion segment situated superior to the injured segment was unaltered by the injury or spacer implantation (see FIG. 12A and FIG. 13). Loading behavior at the implanted level (L2-L3) was identical to the intact condition (see FIG. 13). Total rotation at the injured level rose by 4.5° as a result of the nucleus removal (see FIG. 13). Implantation at the injured level restored total rotation to within 0.5° of the intact case (see FIG. 13), but shifted the loading curve by reducing extension rotation and increasing flexion rotation (see FIG. 12B). Rotation at the L3-L4 and L4-L5 levels was not greatly altered due to injury or implant installation.

The results of this experiment confirmed that the center of rotation of an injured motion segment that was stabilized with the interspinous spacer device was situated in a region consistent with the uninjured segment's center of rotation. In addition, injury to a motion segment resulted in a higher range of motion relative to the uninjured state. Stabilization of the injured segment using the interspinous spacer device restored the range of motion of the injured segment to uninjured levels, with no discernable effect on motion segments situated cranial or caudal to the injured segment.

Example 2

Assessment of the Stress Distribution of an Interspinous Spacer Device

To assess the distribution of stresses acting on an interspinous spacer device during stabilization of a spinal segment, the following experiment was conducted. The finite element model of the injured spinal segment stabilized using an interspinous spacer device similar to the model described in Example 1 was used to determine the stresses acting on the device during applied flexion/extension moments of up to 7.5

Nm. The results of these experiments are presented in FIG. 14 and FIG. 15 for the sliding rod and base of the interspinous spacer device, respectively.

Figure 14:
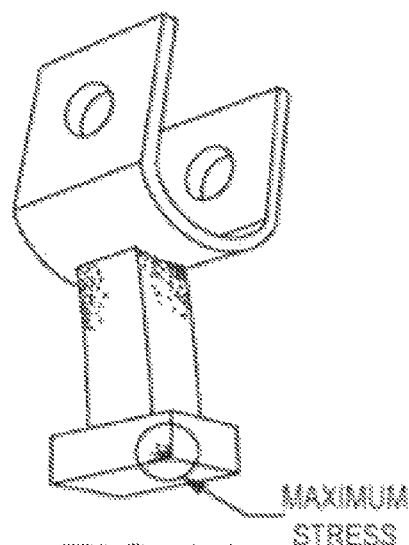
FIG. 14 is an image of a finite element model of a sliding rod of an interspinous spacer device showing the region of maximum stress during flexion.
Figure 15:
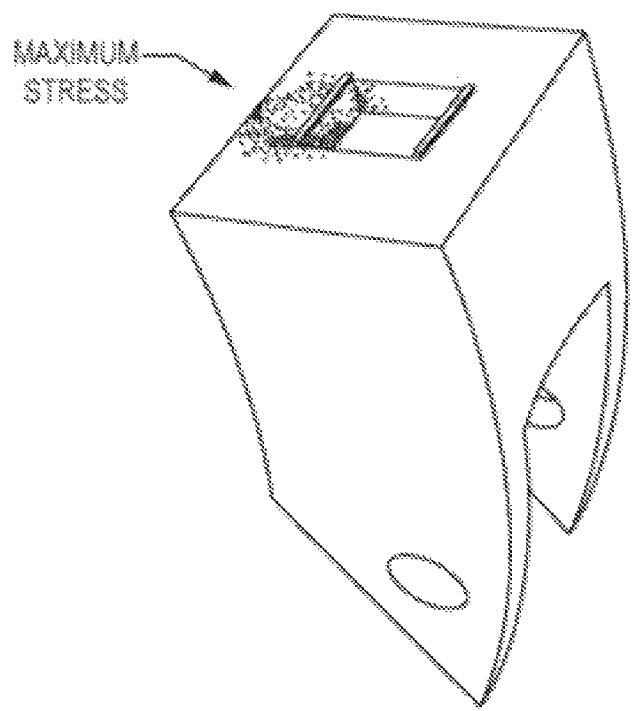
FIG. 15 is an image of a finite element model of a base of an interspinous spacer device showing the region of maximum stress during flexion.

Peak stresses during spinal flexion occurred at the base of the sliding rod, as illustrated in FIG. 14. The maximum von Mises stresses observed in this region were 119 MPa. The peak von Mises stresses in the upper region of the column of the sliding rod near the cranial attachment fitting reached 53 MPa. Peak stresses on the base occurred in the region of the anterior edge of the aperture as illustrated in FIG. 15. Stresses on the base reached a maximum of 27.2 Mpa, which was significantly lower than the stresses observed for the sliding rod. The stress levels on the base fell below the fatigue limit of titanium, indicating that failure of the implant was not likely during loading associated with spinal flexion.

The location of peak stresses on the upper sliding rod occurred at the same location in extension as for flexion. The maximum von Mises stress during extension at the corner of the sliding rod indicated in FIG. 14 was 488 MPa. The stress at the adjacent location on the base piece was 164 MPa. These stresses were deemed unacceptably high for the device to maintain structural integrity over the lifetime of a patient receiving treatment using the device.

The results of these experiments determined that the interspinous spacer device may sustain unacceptably high stress levels during simulated spinal extension, indicating a risk of device failure with the design tested. Modifications to the geometry device to increase the size and amount of material used to produce the interspinous spacer device may reduce the stress levels to within acceptable levels.

Example 3

Figure 16:
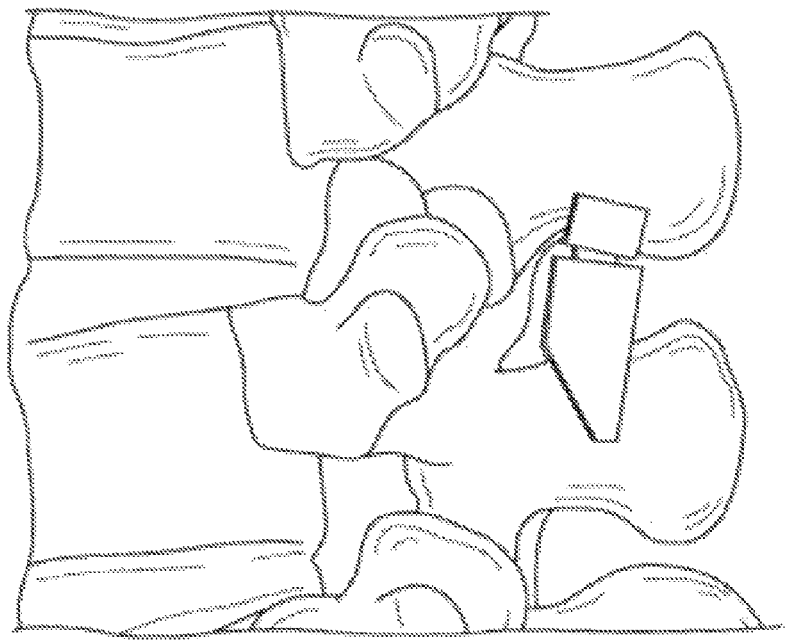
FIG. 16 is an image of a finite element model of an interspinous spacer device with a modified design implanted in a spinal segment.
Figure 17:
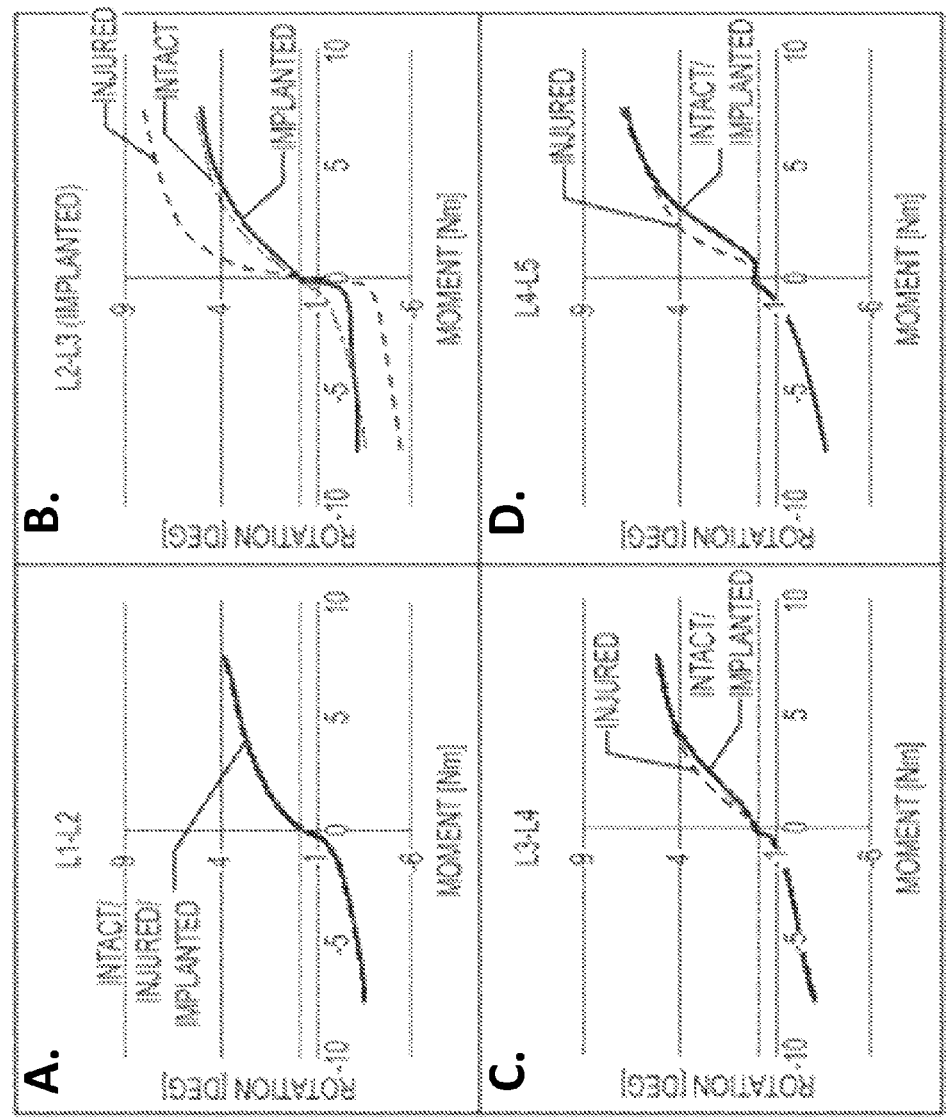
FIG. 17 are graphs showing the relative rotation as a function of applied flexion/extension moment estimated using finite element models during spinal flexion and extension for an intact spine, an injured spine, and an injured spine stabilized with an interspinous spacer device with a modified design implanted at the L2-L3 level for different lumbar spine segment levels: L1-L2 (FIG. 17A), L2-L3 (FIG. 17B), L3-L4 (FIG. 17C), and L4-L5 (FIG. 17D).

Finite Element Assessment of the Range of Motion of a Vertebral Segment Stabilized Using a Revised Interspinous Spacer Device Design To assess the range of motion and center of rotation of a vertebral segment stabilized using a modified interspinous spacer device, the following experiments were conducted. A finite element model of an interspinous spacer device with a modified design relative to the device analyzed in Example 1 was implanted on the spinal segment model as described in Example 1. The finite element model used in these experiments is illustrated in FIG. 16. The center of rotation and range of motion of the modified interspinous spacer device during spinal flexion and extension was assessed using methods and conditions similar to those described in Example 1.

The center of rotation location during flexion and extension of the spinal segment stabilized using the modified interspinous spacer device was comparable to the center of rotation locations observed for the previous design described in Example 1.

FIGS. 17A-D summarize the range of motion as a function of the applied flexion/extension moment for four levels of a spinal segment stabilized using the modified interspinous spacer. The range of motion of the stabilized spinal segment was closer to the range of motion of the intact segment than the range of motion for the previous interspinous spacer shown in FIG. 12. The loading curve for the implanted L2-L3 level shown in FIG. 17B indicated restoration of rotation in flexion and extension that closely corresponded to the intact segment.

Figure 18:
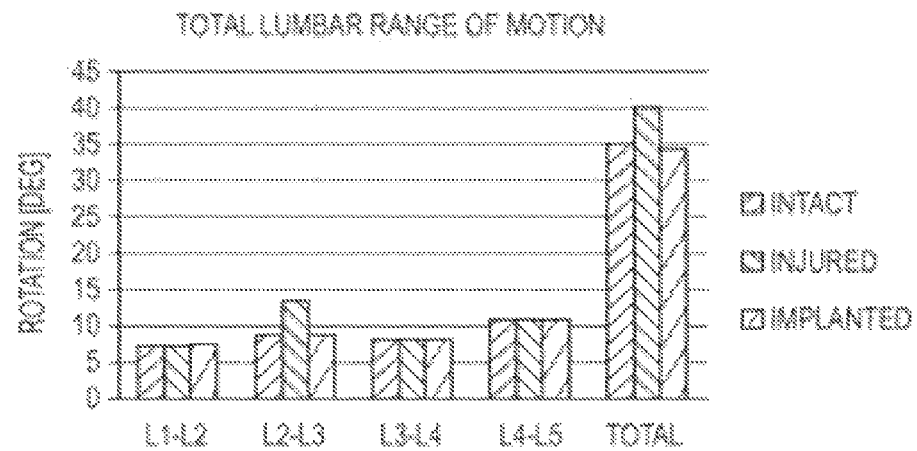
FIG. 18 is a graph comparing the relative rotation of 4 different spinal segment levels and the total rotation estimated using finite element models during spinal flexion and extension for an intact spine, an injured spine, and an injured spine stabilized with an interspinous spacer device with a modified design implanted at the L2-L3 level.

The maximum intervertebral rotations of the four different levels of the spinal segment as well as the total rotation of all segments for the intact, injured, and implanted spine models are summarized in FIG. 18. Intervertebral rotations of the implanted spine returned to within 0.5° of the intact spine for all corresponding spinal segment levels after installation of the modified interspinous spacer device, and the total lumbar rotation returned to within 1.0° with the addition of the device.

The results of this experiment verified that the stabilization of an injured spinal segment using the modified interspinous spacer device resulted in intersegmental rotation angles that were consistent with the intact spine model.

Example 4

Assessment of the Stress Distribution of a Modified Interspinous Spacer Design

To assess the distribution of stresses acting on a modified interspinous spacer device similar to the device described in Example 3 during stabilization of a spinal segment, the following experiment was conducted. The finite element model of the injured spinal segment stabilized using the modified interspinous spacer device described in Example 3 was used to determine the stresses acting on the device during applied flexion/extension moments of up to 7.5 Nm using methods similar to those described in Example 2.

A major goal of the modified interspinous spacer design was to reduce the stresses experienced by the implant in extension, these experiments focused mainly on this loading condition. Further, because the highest peak stresses were observed in Example 2 on the sliding rod of the interspinous spacer device, the peak stresses acting on the sliding rod were of particular interest.

Figure 19:
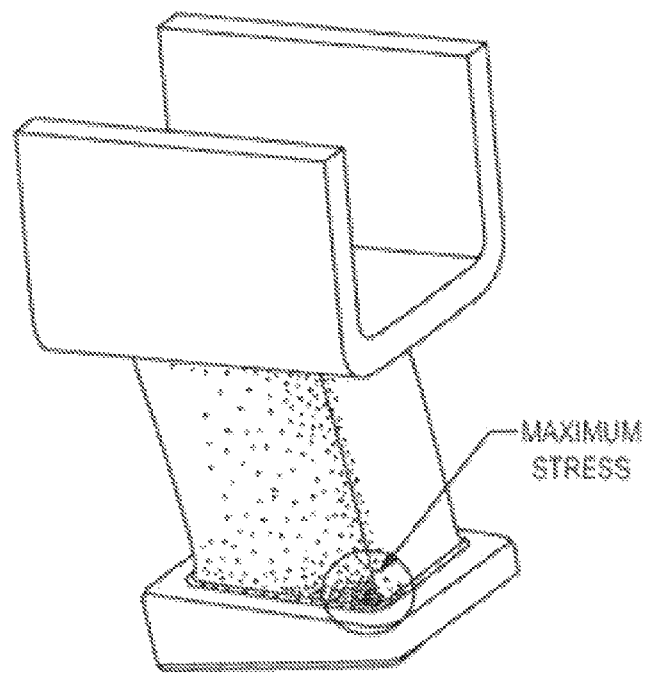
FIG. 19 is an image of a finite element model of a sliding rod of an interspinous spacer device with a modified design showing the region of maximum stress during flexion.

The results of the finite element analysis indicated that the peak von Mises stress on the base of the modified interspinous spacer device was 17 MPa. The peak von Mises stress observed on the sliding rod was 67.1 Mpa, and was situated in a similar location to the peak stress observed in Example 2 (see FIG. 19). These peak von Mises results fell well below the fatigue limit of the Ti6Al4V material from which the modified interspinous device was constructed.

The results of this experiment indicated that the modified design of the interspinous spacer device resulted in significantly lower peak stresses compared to the peak stresses observed for the previous design in Example 2. These results support the conclusion that the modified device would successfully withstand fatigue testing, and posed little risk of failure over a lifetime of use to stabilize a degraded spinal segment of a patient.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. An interspinous spacer device for the stabilization of a degraded spinal segment, the device comprising:
   a base comprising:
      a body containing a curved internal track, wherein the track opens upward into an aperture contained within an upper surface of the body, wherein the aperture has an aperture cross-sectional area that is smaller than a corresponding track cross-sectional area of the curved internal track; and
      a caudal attachment fitting comprising a first caudal attachment plate and a second caudal attachment plate projecting perpendicularly downward from opposite edges of the body of the base; and a sliding rod comprising:
- a retaining plate situated within the curved internal track, wherein the retaining plate has a non-circular cross-sectional shape and a plate cross-sectional area that is larger than the aperture cross-sectional area and smaller than the track cross-sectional area;
- a column comprising an upper column end and a lower column end opposite to the upper column end, wherein the lower column end is attached to the retaining plate and the upper column end protrudes upward through the aperture and out of the upper surface of the body; and
- a cranial attachment fitting comprising a lower plate attached to the upper column end of the sliding rod, and a first cranial attachment plate and a second cranial attachment plate attached to opposite edges of the lower plate, wherein the first and second cranial attachment plates extend perpendicularly upwards from the lower plate;

wherein the non-circular cross-sectional shape of the retaining plate is essentially matched with a cross-sectional shape of the curved internal track such that the retaining plate of the sliding rod freely slides within the curved internal track without significant resistance force to actuate an arcuate movement of the sliding rod along a range of movement limited by a length of the curved internal track, and with a center of rotation of the arcuate movement situated at a perpendicular distance from the track that is equal to a radius of curvature along the length of the curved internal track; and wherein the base is attachable to a caudal spinous process of a vertebra situated caudal to the degraded spinal segment and the sliding rod is attachable to a cranial spinous process of a vertebra situated cranial to the degraded spinal segment.

2. The device of claim 1, wherein the range of movement of the sliding rod is limited to a rotation that is consistent with a physiologically normal rotation of a spinal segment to be stabilized using the interspinous spacer device.

3. The device of claim 2, wherein the range of movement of the sliding rod is limited to a rotation of less than about 10 degrees between a fully extended position and a fully retracted position of the sliding rod in the base.

4. The device of claim 3, wherein the range of movement of the sliding rod is limited to a rotation of about 8 degrees between the fully extended position and the fully retracted position of the sliding rod.

5. The device of claim 1, wherein the center of rotation of the device is situated within a region chosen from: a body of a vertebra within the degraded spinal segment, and a disk within the degraded spinal segment.

6. The device of claim 1, wherein the radius of curvature along the length of the curved internal track is about 50 mm.

7. The device of claim 1, wherein the cranial attachment fitting is attachable to the cranial spinous process by placing the cranial spinous process into a groove formed by the curved lower plate, the first cranial attachment plate, and the second cranial attachment plate and inserting one or more fasteners through the first cranial attachment plate into the cranial spinous process and through the second cranial attachment plate into the cranial spinal process.

8. The device of claim 1, wherein the caudal attachment fitting is attachable to the caudal spinous process by placing the caudal spinous process into a groove formed by the body of the base, the first caudal attachment plate, and the second caudal attachment plate and inserting one or more fasteners through the first caudal attachment plate into the caudal spinous process and through the second caudal attachment plate into the caudal spinal process.

9. An interspinous spacer device for the stabilization of a degraded spinal segment, the device comprising:

a base comprising:
- a body containing a curved internal track bounded at opposite ends by a lower track wall and an upper track wall, and bounded laterally by a curved anterior track wall, a curved posterior track wall, and two side track walls, wherein the curved internal track opens upward into an aperture contained within the track upper wall and extending through an upper surface of the body, wherein the aperture has an aperture cross-sectional area that is smaller than a corresponding track cross-sectional area of the curved internal track; and
- a caudal attachment fitting comprising a first caudal attachment plate and a second caudal attachment plate projecting perpendicularly downward from opposite edges of the body of the base; and a sliding rod comprising:
- a retaining plate situated within the curved internal track comprising an upper surface, a lower surface, an anterior face, a posterior face, and two side faces, wherein the retaining plate has a non-circular cross-sectional shape and a plate cross-sectional area that is larger than the aperture cross-sectional area and smaller than the track cross-sectional area;
- a column comprising a lower column end attached to the upper surface of the retaining plate and an upper column end situated opposite to the lower column end and protruding upward from the upper surface of the body through the aperture of the body; and
- a cranial attachment fitting comprising a lower plate attached to the upper column end of the sliding rod, and a first cranial attachment plate and a second cranial attachment plate attached to opposite edges of the lower plate, wherein the first and second cranial attachment plates extend perpendicularly upwards from the lower plate;

wherein the non-circular cross-sectional shape of the retaining plate is essentially matched with a cross-sectional shape of the curved internal track such that the retaining plate of the sliding rod slides freely within the curved internal track without significant resistance force to actuate an arcuate movement of the sliding rod along a range of movement limited by the track, and with a center of rotation of the arcuate movement situated at a perpendicular distance from the anterior track wall that is equal to a radius of curvature along the length of the curved internal track; and wherein the base is attachable to a caudal spinous process of a vertebra situated caudal to the degraded spinal segment and the sliding rod is attachable to a cranial spinous process of a vertebra situated cranial to the degraded spinal segment.

10. The device of claim 9, wherein the anterior face of the retaining plate slides along the anterior track wall, and the posterior face of the retaining plate slides along the posterior track wall.

11. The device of claim 10, wherein the anterior face, the posterior face, the anterior track wall, and the posterior track wall each have a radius of curvature equal to the radius of curvature of the curved internal track.

12. The device of claim 9, wherein the range of movement is limited to a maximum extension of the sliding rod from the base corresponding to the contact of the upper surface of the retaining plate with the upper track wall.

13. The device of claim 12, wherein the range of movement is further limited to a maximum retraction of the sliding rod into the base corresponding to the contact of the lower surface of the retaining plate with the lower track wall.

14. The device of claim 13, wherein the range of movement between the maximum extension and maximum retraction of the sliding rod is about 3.5 mm.

15. The device of claim 14, wherein the radius of curvature along the length of the curved internal track is about 50 mm.

16. The device of claim 15, wherein the range of movement between the maximum extension and maximum retraction of the sliding rod corresponds to a rotation about the center of rotation of about 8 degrees.

17. The device of claim 9, wherein the column has a radius of curvature equal to the radius of curvature of the track.

18. The device of claim 9, wherein the retaining plate, the column, and the curved internal track have matching non-circular cross-sectional shapes.

* * * * *